United States Patent [19]

Proni

[11] 4,274,552
[45] Jun. 23, 1981

[54] LIQUID DISPENSER

[75] Inventor: Oscar Proni, Hollywood, Fla.

[73] Assignee: Coulter Electronics, Inc., Hialeah, Fla.

[21] Appl. No.: 23,959

[22] Filed: Mar. 26, 1979

[51] Int. Cl.³ .............................................. B67D 5/08
[52] U.S. Cl. ...................................... 222/61; 222/64; 222/424.5
[58] Field of Search ...................... 222/52, 61, 64, 23, 222/394, 397, 424.5

[56] References Cited

U.S. PATENT DOCUMENTS

| 3,602,395 | 8/1971 | Krech | 222/64 |
| 4,106,671 | 8/1978 | Sharples | 222/61 |

FOREIGN PATENT DOCUMENTS

| 2006782 | 7/1971 | Fed. Rep. of Germany | 222/61 |
| 1437738 | 6/1976 | United Kingdom | 222/61 |

Primary Examiner—Joseph J. Rolla
Attorney, Agent, or Firm—Silverman, Cass & Singer, Ltd.

[57] ABSTRACT

A liquid dispenser system for moving a measure of liquid through a conduit from a source container to a receiving container. A branched flow path is defined between a source of pressurized fluid via a first branch sealingly coupled to the source container and a second branch leading communicatively to said conduit at a location between the intake end and the delivery end. A valve is provided to direct the pressurized fluid along one of said first and second branches. A through coil is interposed between said second branch and said conduit. The first branch terminates above the liquid level of the source container. Pressurized fluid is first directed along said first branch causing liquid flow toward the delivery end of said conduit. When flow of the leading liquid is detected, pressurized fluid is directed to the said location along the second branch to split the flowing column of liquid to deliver the portion above the split to the receiving container and the rest back to the source container.

7 Claims, 1 Drawing Figure 4,274,552

LIQUID DISPENSER

FIELD OF THE INVENTION

This invention relates generally to apparatus for measuring and for then dispensing precise quantities of liquid, such as required for performing dilutions thereof, and more particularly to such apparatus that utilizes a pressurized fluid, such as air, operating under a positive pressure for moving the liquid from a source or storage container first along a columnar flow path and next to split the column of source liquid into a portion which may be directed back to the source and a known volume portion delivered to a predetermined location.

BACKGROUND OF THE INVENTION

Analytical procedures commonly require the preparation of dilutions of small quantities of liquids. The diluting operation can be performed manually utilizing calibrated pipettes, burettes, or the like for measuring a precise volume of liquid to be diluted. However, such manual procedures not only are time-consuming, but also give rise to errors in precision and accuracy.

Automated apparatus or equipment for drawing liquid from a source container, measuring a precise quantity of the liquid, and then directing the measured quantity of liquid to a definite location has been provided. Such apparatus or equipment frequently is mechanically cumbersome and complex, and thus subject to breakdown and additionally operates in a manner believed inherently subject to error.

Specifically, some liquid dispensing devices operate by aspiration of liquid drawn through the length of a long feed tube. A miniscus of some shape is formed in the tube at the top of the liquid column, and its shape affects the quantity of liquid that is aspirated at the beginning and end of the aspirating cycle. When only small quantities of liquid are aspirated, the miniscus itself can generate as much as 3 to 4% error in the measured quantity of liquid, which frequently is not acceptable. Moreover, there are response delays in drawing the liquid up the feed tube at the start of the aspirating cycle that create inaccuracies which are amplified for small quantity measurements. Further, the inability to aspirate certain liquids can limit the overall suitability of such dispensing devices.

Other liquid dispensing devices operate by drawing the liquid through the feed tube and into a calibrated cylinder, where the suction force for moving the liquid is generated by moving a piston in the cylinder itself. The reverse movement of the piston subsequently discharges the measured quantity of liquid. However, suction again acts to draw the liquid into the measuring cylinder, which allows for voids or cavities in the measured liquid in the cylinder. This difference between the actual volume of liquid in the cylinder and the volume of the cylinder itself generally is small, but it is amplified when extremely small quantities of liquid are to be measured and dispensed.

An additional problem experienced in both the aspirator and piston types of liquid dispensing devices is the sample carryover from one operating cycle to the next. Where only small quantities of liquid are to be measured and dispensed, the effects of such carryover again can be amplified to reduce the reliability of the measurement and thus the dilution formed from the measured liquid.

SUMMARY OF THE INVENTION

A liquid dispensing device is provided for moving liquid from a source container along a columnar flow path to a delivery location. A precise quantity of liquid is isolated by splitting the column into a delivered portion and preferably, a returned portion. The volume of the delivered portion is known. The column is split by interrupting same by application thereto of a pressurized fluid. The movement of the column from the source along the said flow path is effected by applying the pressurized fluid as a head to a body of source liquid. Sensor means positioned along the column detects the leading end of the column and then operates valve means pressurized fluid control valve means to apply pressurized fluid angularly to the column of source fluid to split the column at a predetermined location. The volume of the split column above said location is known and is delivered. The source liquid below the split can be returned to the source.

DETAILED DESCRIPTION OF THE INVENTION

Figure 1:
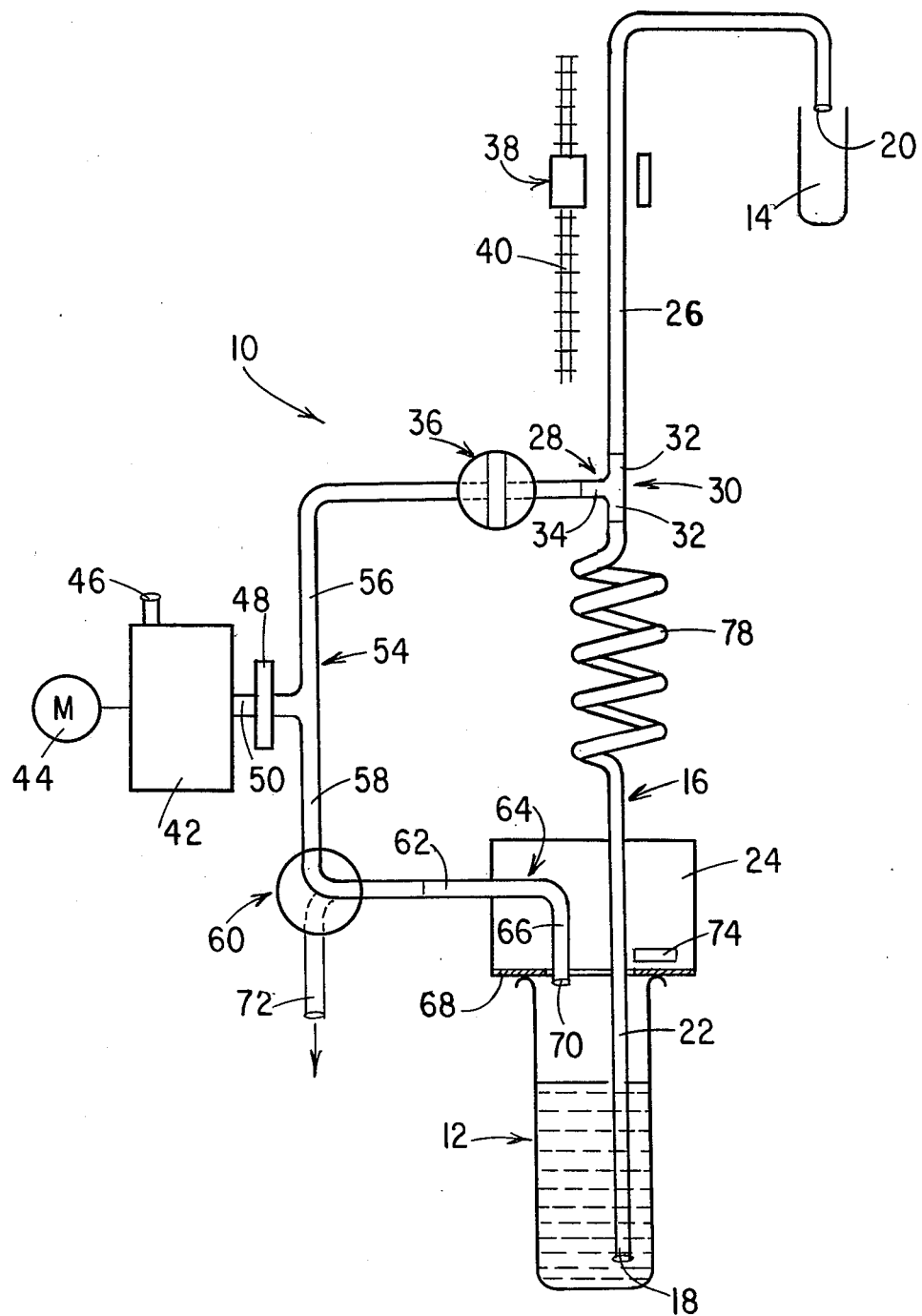
FIG. 1 is a schematic of the pressurized fluid and dispensed liquid flow paths used in subject liquid dispenser, shown in operative association between source and receiving containers.

The liquid dispenser is diagrammatically represented in FIG. 1, and is generally designated by the reference character 10. A container 12 also is illustrated which is adapted to hold the liquid to be measured and dispensed hereinafter referred to as the source liquid, and the illustrated container 14 is used to catch the delivered liquid. The two containers do not form a part of the subject dispensing device, but are shown only in operative association with the device.

The dispenser 10 does include a main liquid carrying conduit 16 which extends continuously between an inlet end 18, and outlet or delivery end 20. The conduit 16 is illustrated with no specific breaks and no distinguishing structural characteristics along its length, but it is contemplated that it may, in fact, have such breaks and be formed of different components.

The conduit is illustrated as fitting in sealed relation through a rubber stopper 24, and it thus presents end section 22 that projects downwardly below the bottom surface of the stopper a distance sufficient to place the inlet 18 within the container 12 and below the level of source liquid therein.

A section 26 of the conduit 16 preferably may be of uniform bore along its length so that the volume contained therein can be determined. Section 26 preferably is transparent, perhaps fabricated of glass. Although it is essential only that the volume of the section be known, or at least capable of being known, appropriate calibration markings or indices can be provided on the exterior surface of the section 26, if desired. Thus, a determinable quantity of liquid can be confined within the section 26 depending upon its length and interior bore diameter.

A T-coupling 28 is interposed at a location 30 along the length of conduit 16 at section 26 thereof. The arms 32 of T-coupling 28 form part of the conduit 16 while the leg 34 is coupled to a valve in the form of stop cock 36.

A sensor 38 which preferably is in the form of a photocell, is located at a predetermined location along section 26 of conduit 16. The sensor 38 is capable of sensing the length end of a column of liquid as it traverses section 26 of conduit 16.

The sensor 38 may be mounted on a track 40 to allow for selective variability of its location along the length of section 26. This allows the volume of liquid within the section 26 between location 30 and the sensor 38 to be varied in order to vary the quantity of liquid that will be delivered, as will be described.

The liquid dispenser 10 includes a source of pressurized fluid, herein illustrated specifically as an air compressor 42 powered by motor 44. The inlet 46 to compressor 42 may open to the atmosphere and consequently a filter 48 preferably is used to remove impurities. Also, a grease filter (not shown) can be provided for the compressor 42. The outlet 50 is connected to a branched tube 54, one leg 56 communicating through stop cock 36 to leg 34 of T-coupling 28. Leg 58 of tube 54 is coupled by way of valve 60 to leg 62 of the angled tube 64. Tube 64 is seated in stopper 24 with leg 66 opening through to surface 68 of stopper 24, as shown at 70. The leg 66 terminates adjacent the surface 68 and hence would be spaced above the normal level of liquid in the container 12. Line 72 leads from valve 60 to the atmosphere for venting purposes, as will be described.

As above noted, preferably the stopper 24 is formed of a resilient material and presents at its downwardly facing or bottom end an annular seating surface which surrounds the section 22 of the conduit 16 and the open end of line 66. The source container 12 would have an annular seating rim which cooperates with bottom surface 68 to enable an airtight seal to be established between the removable container 12 and the stopper 24.

The valve 60 operates between a first operative position whereat the output from the compressor 42 is directed from the leg 58 to leg 62 of tube 64, and a second operative position whereat the inflow from the compressor is blocked and the container 12 is vented to atmosphere via line 72.

The stopcock 36 and valve 60 operate somewhat in tandem so that pressurized fluid either is directed to leg 34 or to leg 62. All that is required for dispensing a known volume of liquid is that the interior volume of the intermediate section be known or determined between the location at which the leading end of the flowing column is sensed and the break off point 30.

Pressurized fluid is directed to the column of source liquid to split the column into two portions, the first comprising the liquid in the column above the point of interruption (break point) and all liquid below said point. The source liquid above the break point can be determined either by knowledge of the interior volume of the intermediate section for the length of the column above the break point; or by measuring the column length above the break point and, with the interior bore of said conduit portion uniform, determining the volume encompassed by that length of column.

In the preferred embodiment of the invention, the valve 36 normally is biased in its blocking condition to prevent passage of pressurized fluid to location 30 along conduit 16. Valve 60 normally is biased to establish communication to the outlet of leg 66. Conventional electrical or pneumatic control means may be employed to operate said valves along with suitable linkages between the sensors and said functioning controls and elements.

A sensor 74 may be located adjacent the stopper 24 in an appropriate position to sense the presence of a container 12 properly sealingly seated against the stopper 24. The sensor 74 may have an actuator which might be in the form of a thin leaf spring feeler (not shown) located crosswise of the annular seating surface on the stopper. Thus, when a container 12 is pressed against the stopper 24 and urged into sealing relationship therewith, the feeler is tripped to energize the compressor 42 and thus initiate a measuring and dispensing cycle.

Included in the configuration of conduit 16 is a coiled section 78 for the purpose of adding internal resistance to the flow of liquid therethrough. Section 78 is located between location 30 and the inlet end 18 of conduit 16. The resulting internal resistance serves generally to equalize the respective flow resistances of the liquid moving through the conduit 16 upstream and downstream of location 30 until the slug of liquid is discharged from the delivery end 20 of conduit 16 into container 14.

OPERATION OF THE SUBJECT INVENTION

In order to operate the subject liquid dispenser 10, the user would position a container 14 at the outlet end 20 of the conduit 16 and would subsequently position the source container 12 adjacent the stopper 24. The container 12 is urged against surface 68 of stopper 24 to effect a seal therebetween. Sensor 74 is activated by such engagement to energize compressor 42. The output of pressurized fluid from compressor 42 is directed to leg 62 via the valve 60 to pressurize the interior of the container 12 and act as a pressure head upon the liquid in the container 12 to force source liquid through inlet 18 of conduit 16 along section 22 and coiled to within the section 78 past arms 32 of T-coupling 28 and along section 26 of conduit 16. At the location of the sensor 38, the passage of leading end of the column of source liquid presence will be sensed. The valves 36 and 60 will be operated to apply the pressurized fluid to location 30 interrupting the column of source liquid at said location.

Valve 60 effectively blocks flow from the compressor 42 to leg 62 and vents the container 12 to atmosphere. Valve 36 allows the fluid flow through the inlet 30 of the tee connection 28 into the conduit means 16. The surge of pressurized fluid via leg 34 interrupts or severs the liquid column traversing conduit 16. The slug of liquid located downstream between the location at which the sensor 38 senses the arrival of the head of said flowing liquid column and location 30, the "break point", has a determinable volume and is driven to and from delivery end 20. The portion of the liquid column below location 30 is forced back through coil 78 toward inlet opening 18 and into the container 12.

When it has been determined that the slug of liquid located in section 26 between the head of the column and the break point 30, has been conveyed along the conduit 16 until it is discharged via outlet 20 into the container 14, the operator can detect that the conduit 16 has been emptied and the measured quantity of liquid has been dispensed. Then, container 12 can be separated from the stopper 24. At this time, or perhaps just prior to separation, the valves 36 and 60 can be operated to return to their initiate condition, and/or the motor 44 may be deenergized to terminate the operation of the compressor 42.

The air flow from the T-coupling 28 in both directions along the conduit 16 effectively flushes out the conduit for removing sample traces and readies the dispensing device for the next cycle.

Minor modifications may be made in construction and arrangement of the described elements without departing from the spirit and scope of the invention as defined in the appended claims.

What I claim is:

1. A liquid dispenser for drawing a calibrated quantity of liquid from a source container and for dispensing same at a location distant from the container, comprising a conduit having an inlet end opening adapted to be located below the level of the liquid in the container and having an outlet end opening located at said location, said conduit having an intermediate portion of known interior volume to provide determinable volumetric confinements of liquid therein, a source of fluid under pressure, first and second flow path means connecting the pressurized fluid source both to the container, and to said conduit angularly thereto at a first location along said intermediate portion thereof, respectively, means effecting a sealed coupling between the source container and the inlet end of said conduit, sensor means at a second location proximate said intermediate portion and operable to sense the leading end of said flowing liquid at the second location along said intermediate portion, first and second valve means interposed in said first and second flow path means, respectively, whereby alternatively to direct pressurized fluid to the container to apply a pressure head to the liquid therein whereby to force the liquid through said inlet end along said conduit toward the outlet end thereof past the intermediate portion and to direct pressurized fluid only to said conduit at said first location along said intermediate portion effective thereby to interrupt the liquid flow therein and to drive that liquid located between the second location and the interrupted first location toward the outlet end opening of the conduit and said first and second valve means being operatively coupled to said sensing means to effect said interruption and driving.

2. The liquid dispenser as claimed in claim 1 in which the remaining liquid in the said conduit is directed back toward the inlet end opening of the conduit to the container.

3. The liquid dispenser according to claim 1 in which the intermediate portion has a uniform interior diameter bore along the length thereof.

4. A liquid dispenser according to claim 1, in which said means for effecting the seal includes a resilient elastomeric stopper coupled to said conduit and said fluid flow path means, said stopper including a surface capable of receiving the upper end of the source container sealingly to be engaged thereagainst.

5. A liquid dispenser according to claim 1 in which said sensor means comprises a photodetector device, said conduit being capable of transmitting light therethrough.

6. A liquid dispenser according to claim 1 in which said conduit includes a coiled portion between said location and the inlet end opening, effective thereby to approximate the resistance of liquid flow therethrough to the resistance of liquid flow through the conduit downstream of said location.

7. A liquid dispenser according to claim 1 wherein said sensor means are adjustably positioned along the length of said intermediate portion whereby the point of interception of said leading end is selectively variable.

* * * * *